United States Patent [19]
Broom et al.

[11] Patent Number: 6,130,324
[45] Date of Patent: Oct. 10, 2000

[54] AMPHIPATHIC OLIGONUCLEOTIDES AND POLYNUCLEOTIDES HAVING POTENT ANTIVIRAL ACTIVITY

[75] Inventors: Arthur D. Broom; Robyn Thorpe, both of Salt Lake City, Utah

[73] Assignee: University of Utah Research Foundation, Salt Lake City, Utah

[21] Appl. No.: 09/371,909

[22] Filed: Aug. 10, 1999

Related U.S. Application Data

[60] Provisional application No. 60/096,058, Aug. 11, 1998.

[51] Int. Cl.$^7$ .................................................. C07H 21/00
[52] U.S. Cl. ...................... 536/23.1; 536/25.3; 536/25.5
[58] Field of Search ................................ 536/23.1, 24.1, 536/24.5, 24.31, 24.33, 24.3, 25.3, 25.35; 435/91.5, 6

[56] References Cited

U.S. PATENT DOCUMENTS

| | | | |
|---|---|---|---|
| 4,024,222 | 5/1977 | Ts'o et al. | 424/180 |
| 4,130,641 | 12/1978 | Ts'o et al. | 424/85 |
| 4,711,955 | 12/1987 | Ward et al. | 536/29 |
| 5,063,209 | 11/1991 | Carter | 514/44 |
| 5,652,359 | 7/1997 | Meyer, Jr. et al. | 536/25.5 |

FOREIGN PATENT DOCUMENTS

97/26270  1/1997  WIPO .

OTHER PUBLICATIONS

Kaufmann et al. "Monofunctional Substrates of Polynucleotide Phosphorylase" Eur J Biochem 24:4–11, 1971.

Tutonda et al., "The Role of Hydrophobic Versus Hydrophilic Base Character in the Anti–HIV Activity of Purine–Containing Polyribonucleotides", Nucleosides & Nucleotides (1996), pp. 173–182.

Chan et al., "Antiviral Properties of Polyinosinic Acids Containing Thio and Methyl Substitutions", J. gen. Virol. (1981), pp. 291–299.

Broom et al., "Unusual Single–Stranded Polyribonucleotides as Potent Anti–HIV Agents", Journal of Medicinal Chemistry (1995), pp. 3253–3257.

Tutonda et al., "Antiviral Oligo–And Polyribonucleotides Containing Selected Triazolo[2,3–a]Purines", J. Med. Chem (1998), pp. 4958–4964.

Buckheit et al., "PMTI, A Broadly Active Unusual Single–Stranded Polyribonucleotide, Inhibits Human Immunodeficiency Virus Replication By Multiple Mechanisms", Antiviral Chemistry & Chemotherapy (1999), pp. 23–32.

Amarnath et al., Polyribonucleotides Containing Thiopurines Synthesis and Properties of Poly(1–Methyl–6–Thioguanylic Acid), Biochimica et Biophysica Acta (1977), pp. 16–23.

*Primary Examiner*—George C. Elliot
*Assistant Examiner*—Karen Lacourciere
*Attorney, Agent, or Firm*—Madson & Metcalf

[57] ABSTRACT

The present invention provides novel compositions that show potent antiviral activity against both DNA and RNA viruses. In particular, the present invention provides oligo- and polyribonucleotides with potent antiviral activity against HIV and HCMV. These compositions are thought to operate in a novel fashion at an early stage of viral infection, meeting the need for alternatives or synergistic therapies to the toxic treatments currently available. The present invention also discloses methods for synthesizing oligo- and polyribonucleotides showing antiviral activity.

20 Claims, No Drawings

AMPHIPATHIC OLIGONUCLEOTIDES AND POLYNUCLEOTIDES HAVING POTENT ANTIVIRAL ACTIVITY

RELATED APPLICATIONS

This application is related to and claims the benefit of United States Provisional Application Ser. No. 60/096,058 of Arthur D. Broom and Robyn M. Thorpe filed Aug. 11, 1998 and entitled Amphipathic Oligonucleotides and Polynucleotides Having Potent Antiviral Activity, which is incorporated herein by this reference.

FIELD OF THE INVENTION

The present invention relates to compositions and methods of making oligonucleotides and polynucleotides for treating infections by RNA and DNA viruses. More specifically, the present invention relates to amphipathic oligonucleotides and polynucleotides that show broad-spectrum activity against retroviruses such as the human immunodeficiency virus and DNA viruses such as human cytomegalovirus.

TECHNICAL BACKGROUND

Acquired Immunodeficiency Syndrome, commonly known as AIDS, is a disease that currently plagues millions of people worldwide. Scientists isolated human immunodeficiency virus (HIV), the virus that causes AIDS, in 1983, and have tried to develop cures and therapies for this devastating virus. Unfortunately, there is no known cure. Research has produced a number of drugs that treat the disease in the hopes of prolonging the length and quality of life for HIV-infected individuals. HIV infection, however, is particularly difficult to treat because the virus rapidly mutates into different forms, and each form may respond differently to drugs and therapies. As a result, scientists have developed a number of different drugs that attack HIV in different ways, although new and effective treatments are desperately needed.

To understand how current HIV treatments work, it is helpful to know how HIV reproduces. HIV is an RNA virus, that is, its genes are coded on strands of RNA. The first step in the life cycle of HIV is the virus's entry into a host cell. In the second step, HIV makes a DNA copy of its genes from the RNA template using a viral enzyme called reverse transcriptase. Third, the DNA copy of the viral gene is inserted into the host cell's own DNA genes. This means that the infected cell now has both its own DNA and HIV DNA in its genome. Cells prepare RNA copies of the DNA in their genes by a process known as "transcription," and so the fourth step involves transcribing RNA—not only from the host cell's own DNA, but from the viral DNA that has become part of the host cell's genome. Some of this newly transcribed RNA is the genetic material that goes into new HIV viruses, while other viral RNA is used in the fifth step to make proteins and enzymes that enable the creation of new HIV viruses. Sixth, new viruses are assembled in the cell using the viral RNA and the proteins and enzymes that the cell has produced. Lastly, newly formed HIV viruses leave the host cell to infect other cells and continue multiplying.

Twelve drugs are currently approved in the United States for treating HIV; each one fights the virus in a different fashion. These drugs fall into two general categories-reverse transcriptase inhibitors and protease inhibitors.

Reverse transcriptase inhibitors attack the second step of the virus's life cycle, that is, when the virus makes a DNA copy of its RNA genome using reverse transcriptase. Reverse transcriptase takes the building blocks of DNA, called nucleotides, and bonds them together (through a phosphodiester linkage) in a specific sequence using the viral RNA as a template. The resulting DNA is called a "provirus," which is inserted into the host cell's genome. However, as the reverse transcriptase makes DNA from the RNA, it often makes mistakes. It is these "mistakes" that create so many different forms of HIV, making it harder to develop effective treatments. However, it is precisely this tendency to make mistakes that enables scientists to treat HIV with inhibitors of reverse transcriptase. For example, many reverse transcriptase inhibitors operate through defective nucleotides that reverse transcriptase uses in building viral DNA. When reverse transcriptase inserts these defective nucleotides into the growing DNA chain, the defective nucleotides are unable to bond with other nucleotides and so the enzyme stops building the chain. The result is that reverse transcriptase cannot make a complete viral DNA molecule.

These defective nucleotides are called dideoxynucleotides, literally, nucleotides without two oxygens. One of the most successful dideoxynucleosides is azidothymidine (AZT). AZT has a benefit in that HIV reverse transcriptase incorporates AZT into the growing viral DNA, while the host cell's own DNA-generating machinery does not incorporate this defective nucleotide. This enables the replication of host cell DNA to continue relatively unaffected by the presence of AZT.

Other forms of reverse transcriptase inhibitor do not operate by providing defective nucleotides to the RT. Instead, such inhibitors bind to a certain part of the enzyme when it is complexed to DNA. It is believed that this slows down the rate at which the viral DNA is made. Unfortunately, resistant reverse transcriptase has been identified.

The main drawback of reverse transcriptase inhibitors in general, and AZT in particular, is that they can be extremely toxic to the person under treatment. Therefore their dosage must be limited and monitored. In addition, HIV can mutate to create viruses that are resistant to these treatments. Consequently, patients now take combinations of dideoxynucleotides to reduce the chance of developing drug resistant forms of HIV. New treatments that could reduce the patient's reliance on these toxic treatments are desperately needed.

In contrast to nucleoside and non-nucleoside inhibitors of reverse transcriptase, HIV protease inhibitors target the fifth step of the virus's life cycle—when the virus causes the host cell to make proteins that are used in assembling new viruses. HIV protease is a viral enzyme that cuts large proteins (called "polyproteins") produced from viral genes into smaller proteins, such as viral coat proteins and viral enzymes, including reverse transcriptase and the viral protease. HIV protease selectively binds to a site on the polyprotein to be cut (the "substrate"), and then cuts the polyprotein in to smaller proteins. HIV protease inhibitors are effective because the protease will bind with the inhibitor, and attempt to cut it. However, the inhibitor cannot be cut and stays bound to the protease. In doing so, the true substrates cannot gain access to the enzyme. If the polyproteins are not cut, then the smaller proteins necessary for the synthesis and assembly of viral particles are not formed. The resultant defective virions prevent further HIV infection.

Despite recent advances in combination chemotherapy using both reverse transcriptase and protease inhibitors, no cures are claimed and resistance is beginning to develop. New drugs having unique structures and targets are desperately needed.

People with AIDS typically suffer infection by opportunistic organisms. One such organism is human cytomegalovirus ("HCMV"). HCMV is a DNA virus; that is, HCMV's genome is a DNA molecule. HCMV is most commonly seen in AIDS victims and is believed to take advantage of the victim's weakened immune system. HCMV infections often lead to death or severe disease, such as blindness. At present, very few drugs have proven effective, but current treatments include ganciclovir, foscarnet, and cidofovir. Similar to HIV, HCMV makes DNA copies of its genome once it has infected the host cell. Unlike HIV, HCMV uses its genetic DNA as a template, and uses an enzyme called a polymerase to make the new DNA chains. Both ganciclovir and cidofovir operate by binding to this polymerase and causing a slowing and eventually stopping the DNA chain elongation when incorporated into the viral DNA.

By contrast, foscarnet does not incorporate into the growing viral DNA chain, but instead blocks a binding site of the polymerase, inhibiting the growth of the DNA chain. Unfortunately, none of these treatments provides a cure for HCMV, and all have significant drawbacks. These treatments can be very toxic, and drug resistant strains of HCMV develop within a relatively short period of time through mutations in one or more of the virus's genes. As will be readily appreciated, novel treatments against DNA viruses generally, and human cytomegalovirus in particular, are desperately needed.

Relatively recently, polyribonucleotides and oligoribonucleotides containing sulfur have been shown to be potent against both HIV and HCMV. Regarding HIV, the working hypothesis is that these drugs bind to and fill the RNA-binding site on reverse transcriptase. The method of DNA antiviral activity is not yet known, but it is thought that the amphipathic character (hydrophobic, or water-fearing, base and hydrophilic, or water-loving, backbone), and the ability to form a highly ordered structure in solution are prerequisites to antiviral activity. The drawback of these compounds is that they are not readily made via chemical or enzymatic techniques, and it is believed that they rely on secondary structure in solution for antiviral activity.

Consequently, it would be a great advancement in the art to provide treatments with potent broad spectrum antiviral activity against both DNA viruses and RNA viruses. It would be a further advancement in the art to provide a composition showing antiviral activity against HIV. Still another advancement in the art would be to provide a composition showing antiviral activity against HCMV. Finally, it would be a great advancement in the art to provide compositions that show potent activity against both HIV and HCMV, thereby reducing the reliance on toxic treatments now in use, and decreasing the chance of creating resistant strains of HIV and HCMV.

Such compositions and their methods of manufacture and use are disclosed herein.

BRIEF SUMMARY OF THE INVENTION

The present invention relates generally to oligoribonucleotides and polyribonucleotides that show potent antiviral activity against both HIV and HCMV. The novel oligo- and polyribonucleotides are polymers of a number, n, of nucleoside monomers that may be represented by the formula:

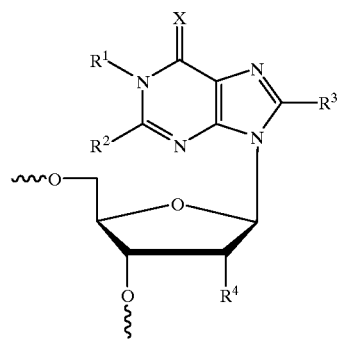

where X is O or S, $R^1$ is a member selected from the group consisting of alkyl, aralkyl, cycloalkyl and unsaturated alkyl; $R^2$ and $R^3$ are independently selected from the group consisting of H, $SCH_3$, $NH_2$, alkylthio, and alkylamino; $R^4$ is a member selected from the group consisting of hydroxy, fluoro, alkoxy, mercaptoalkyl, alkoxyalkoxy, hydroxyalkoxy, and aminoalkoxy; n is an integer of about 12 to 1000; and the monomers are joined by phosphodiester or phosphorothiote linkages. As can be seen, these oligo and polyribonucleotides are comprised of nucleotide chains containing modified purine bases chemically bound to modified ribose sugar backbones.

Compositions containing an oxo group at the 6 position of the purine analog are presently preferred, primarily because they are easier to synthesize. In addition, nucleotides that are 32 units or more in length are also presently preferred as biological activity decreases significantly at chain lengths less than 32.

An illustrative composition according to the invention is poly(1-propargylinosinic acid), wherein X is O; $R^1$ is propargyl; and $R^2$, $R^3$, and $R^4$ are H. Poly(1-propargylinosinic acid) is a polymer of a number, n, of nucleoside monomers that have the following formula:

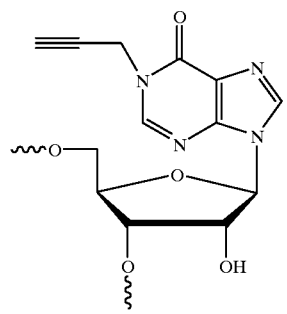

wherein n is an integer from 12 to 1000 and the monomers are all connected by phosphodiester linkages.

As will be shown, these ribonucleotides show inhibitory activity against various strains of HIV at doses that may be reasonably administered to a patient. They also show inhibitory activity against HCMV at doses that are significantly less than the currently preferred treatment, ganciclovir. Such antiviral activity makes these compounds promising in the fight against HIV and HCMV.

The present invention also relates to methods of making novel oligo- and polyribonucleotides, with steps generally comprising synthesis of the modified nucleotides and subsequent polymerization or oligomerization. An illustrative synthesis of poly(1-propargylinosinic acid) comprises the steps of:

(a) reacting propargyl bromide, 1,8-diazabicyclo[5.4.0]undec-7-ene, and inosine to produce 1-propargylinosine;

(b) converting 1-propargylinosine to 1-propargylinosine-5'-monophosphate;

(c) converting 1-propargylinosine-5'-monophosphate to 1-propargylinosine-5'-diphosphate; and (d) polymerizing 1-propargylinosine-5'-diphosphate with polynucleotide phosphorylase to produce poly(1-propargylinosinic acid).

Lastly, the present invention also relates to pharmaceutical compositions which include the novel oligo- and polyribonucleotides, and to a method of treating an infection by a retrovirus or DNA virus in animals, including humans, by administering an effective amount of the composition to patients.

DETAILED DESCRIPTION OF THE INVENTION

As discussed above, the present invention relates generally to compositions that show antiviral activity against both the RNA virus HIV, and the DNA virus HCMV. Specifically, the compositions of the present invention are oligo- and polyribonucleotides with modified purine bases and/or modified ribose sugars, that are linked as shown:

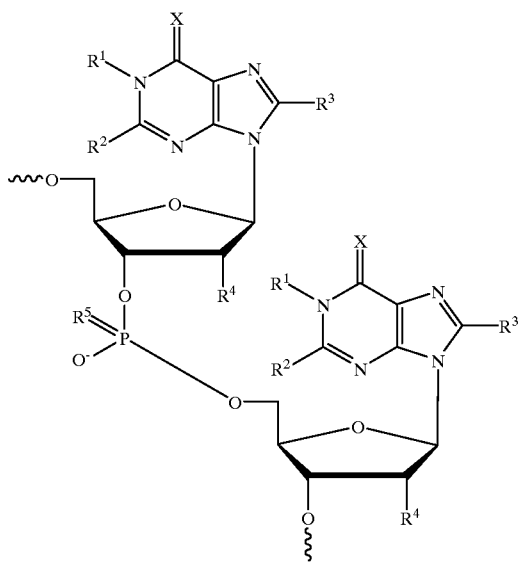

wherein X is O or S, $R^1$ is a member selected from the group consisting of alkyl, aralkyl, cycloalkyl and unsaturated alkyl; $R^2$ and $R^3$ are independently selected from the group consisting of H, $SCH_3$, $NH_2$, alkylthio, and alkylamino; $R^4$ is a member selected from the group consisting of hydroxy, fluoro, alkoxy, mercaptoalkyl, alkoxyalkoxy, hydroxyalkoxy, and aminoalkoxy; $R^5$ is O or S. These compositions are polymers of a number, n, of nucleoside monomers, where n is an integer of about 12 to 1000. Where $R^5$ is O, the bond is a phosphodiester linkage. Where $R^5$ is S, the linkage is a phosphorothioate linkage.

The term "polynucleotide" is used herein to refer to those nucleotide sequences prepared by enzymatic techniques, for example, by using the enzyme polynucleotide phosphorylase (PNP) to polymerize the 5'-diphosphates. PNP can be obtained from a variety of sources, but usually from E. coli or M. luteus, and such enzymes are commercially available, for example, from SIGMA-Aldrich Company, St. Louis, Mo. These polymers are generally greater than 50 monomer units (or bases) in length. They typically range from about 100 to 1000 monomers (approximately 30,000 to 300,000 daltons in weight), but are frequently around 300 to 350 monomer units in length (approximately 100,000 daltons in weight). Presently, the 100 to 1000 unit polymers are preferred. More preferably, such polynucleotides are 300 to 350 monomer units in length.

The term "oligonucleotide" is used herein generally to describe those nucleotide sequences prepared by standard chemical nucleic acid synthetic techniques, for example by using an ABI synthesizer. Such preparation techniques generally yield oligomers from 2 to 100 monomer units (or bases) in length. More preferably, the oligonucleotides of the present invention range form 12 to 40 monomer units in length, and ideally they are 28 to 36 monomer units in length (approximate molecular weight of 10,000 daltons).

The oligo- and polyribonucleotide compounds are readily water soluble and may be administered by the intravenous, intra-ocular, intra-peritoneal, intra-nasal, intramuscular or subcutaneous route, or in a suitable delivery system according to methods well known in the art.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, "effective amount" means an amount of a drug or pharmacologically active agent that is nontoxic but sufficient to provide the desired local or systemic effect and performance at a reasonable benefit/risk ratio attending any medical treatment.

A distinguishing feature of the oligo- and polyribonucleotides of the present invention is that they contain modified nucleotides with substitutions on the base and/or the sugar backbone. The purine analog base may be modified in the 1-N, 2, 6, and/or 8 positions. The 1-N position may contain an alkyl, aralkyl, cycloalkyl, or unsaturated alkyl. The 2 and 8 positions may contain groups independently selected from H, $SCH_3$, $NH_2$, alkylthio, or alkylamino substituents. The 6 position may contain a thio or an oxo group. In addition, the sugar may be ribose or an analog of ribose containing a hydroxy, flouro, alkoxy, mercaptoalkyl, alkoxyalkoxy, hydroxyalkoxy, and aminoalkoxy at the 2' position.

Referring to the general formula of the oligo- and polyribonucleic acids, X may designate either a thio group (S) or an oxo group (O) at the 6 position of the purine analog. While both analogs are within the scope of the present invention, those containing an oxo group are presently preferred as they are readily prepared by enzymatic and/or chemical syntheses. In similar fashion, $R^5$ may also designate an oxo or a thio group, creating either a phosphate or a phosphorothioate, respectively, at the 3' position of the ribose analogs. The present invention contemplates that both types of groups at the 3' position may be present within the same oligo- or polyribonucleotide, but it is presently preferred that each oligo- or polyribonucleotide contains only one of the two groups (either oxo or thio). In this regard, it is known that phosphorothioate linkages tend to increased the stability of nucleotides against nuclease enzymes. Consequently, one preferred embodiment of the present invention contains all thio groups at the position designated $R^5$. Another embodiment is presently preferred where $R^1$ is an unsaturated alkyl, X at the 6 position is an oxygen, and $R^5$ is oxygen. Such compounds are readily synthesized and show biological activity.

More specifically, and in accordance with the present invention, the composition poly(1-propargylinosinic acid) is preferred wherein X is O; $R^1$ is propargyl; $R^2$, $R^3$, and $R^4$ are H; and $R^5$ is O. The monomers are linked as shown below:

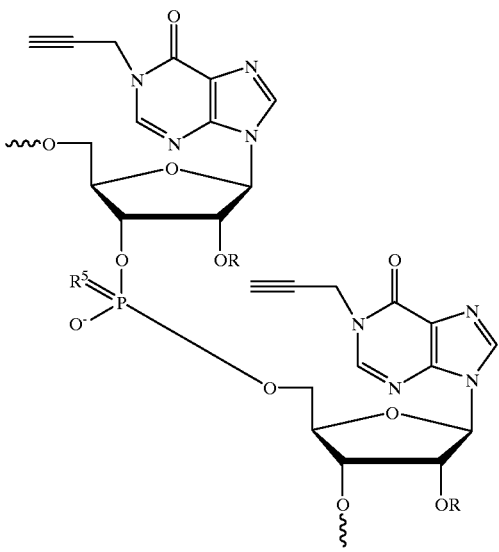

Poly(1-propargylinosinic acid) is an oligo- or polyribonucleotide with oxygen at both the 6 position of the purine analog and at the position labeled $R^5$ within the phosphodiester group. Unlike certain sulfur-containing polyribonucleotides that have been described previously, these molecules with an oxo group at the 6 position are very readily prepared by enzymatic and/or chemical syntheses. Cf. A. D. Broom et al. (1995), *J Med. Chem.* 38:3253–3257; M. G. Tutonda et al. (1998), *J Med. Chem.* 41:4958–4964; U.S. Pat. No. 5,652,359. In particular, enzymatic polymerization proceeds far more rapidly and with much less enzyme than the polymerization of thiopurine analogs.

In accordance with the present invention, all nucleotide linkages in an oligo- or polyribonucleotide may have the same structure, and these "homooligoribonucleotides" and "homopolyribonucleotides" are preferred for certain purposes. However, it will be readily appreciated by those skilled in the art that chains of nucleotides may be synthesized in which not all nucleotides have the same formula, known as "heterooligonucleotides" and "heteropolynucleotides." Such nucleotides are also within the scope of the present invention.

The heterocyclic base, a purine analog, is attached to the sugar moiety, a ribose analog, by a glycosidic (carbon-to-nitrogen) bond, forming nucleosides that may be phosphorylated to nucleotides. Each sugar molecule includes two derivatized hydroxyl groups at the 3' and 5' positions, respectively. The derivatized hydroxyl groups link each nucleotide unit to the adjacent nucleotides with phosphodiester ($R^5$=O) or phophorothioate diester ($R^5$=S) bonds. It is in this fashion that the linked ribose analogs form the hydrophilic sugar backbone, with hydrophobic bases (purine analogs) extending from the backbone. This hydrophilic backbone of the molecule contrasts with the hydrophobic purine analogs to give the oligo- or polyribonucleotides their amphipathic character. This amphipathic character probably plays a role in the antiviral activity of the oligo- and polyribonucleotides of the present invention.

Referring to the glycosidic bonds of the present invention, they may be of either of alpha or beta configuration. The designation of alpha or beta for the configuration of the glycosidic bond is well established and readily understood by those skilled in the art.

Nucleotide chains like the oligo- and polyribonucleotides of the present invention are generally synthesized in the 3' to 5' direction by chemical means, or in the 5' to 3' direction by polymerase enzymes as described below. The groups at the 3' and 5' ends of the completed polymers may depend on the method of synthesis. In certain embodiments of the present invention, various functional groups may be placed at the 3' end of the oligo- or polyribonucleotide. In certain embodiments, hydroxyl groups are the 3' end groups. In another embodiment, cholesterol groups, which facilitate polynucleotide absorption, are attached to the 3' end. Cholesterol groups may be placed at the 3' end of the chain by methods disclosed in, for example, Letsinger et al. (1989), *Proc. Nat'l. Acad. Sci. USA* 86:6533–6536. In yet another embodiment, fluorescent labeling groups are attached to the 3' end to aid in tracking the absorption of the oligo- or polyribonucleotides, and these groups are readily substituted by methods well known in the art. In similar fashion, various functional groups may be placed at the 5' end of the oligo and polyribonucleotides of the present invention. In certain embodiments, hydroxyl groups are preferred. In another embodiment, cholesterol groups are attached to the 5' end, as such groups facilitate polynucleotide absorption. Cholesterol groups may be placed at the 5' end of the chain by methods disclosed in, for example, Desjardins et al. (1995), *J. Drug Targeting* 2:477–485. In yet another embodiment, flourescent labeling groups are attached to the 5' end to aid in tracking the absorption of the oligo- and polyribonucleotides, and these groups are readily substituted by methods well known in the art.

All publications, patents, and patent applications cited in this application are hereby incorporated by reference.

EXAMPLES

The following examples are given to illustrate various embodiments which have been made within the scope of the present invention. It is to be understood that the following examples are neither comprehensive nor exhaustive of the many types of embodiments which can be prepared in accordance with the present invention.

Example 1

Synthesis of 1-propargylinosine

Propargyl bromide (11.8 ml, 105.9 mmol) and 1,8-diazabicyclo[5.4.0]undec-7-ene (20.62 ml, 135.2 mmol) were added to a suspension of inosine (27.56 g, 102.8 mmol) in dimethylacetamide (590 ml). The reaction mixture was stirred at room temperature overnight under argon, at which time TLC in chloroform/methanol (85:15) demonstrated disappearance of starting material. The reaction was terminated by addition to the suspension 3.5 L of ether/hexane (1:1) with storage at about −20 degrees C. overnight. While still chilled, solvent was decanted from the resulting gum, which was then dissolved in methanol and evaporated in vacuo (oil pump) onto silica gel. The product was isolated by silica gel chromatography using chloroform/methanol (95:5). The product was then characterized using mass spectrometry and proton NMR data. The mass spectrometer gave the following results: FABMS(glycerol), m/z 307 (MH+). The NMR data gave the following results: $^1$H-NMR (DMSO-$d_6$): 8.50 (1H, s, H2); 8.39 (1H, s, H8); 5.87, 5.84 (1H, d, H1'); 5.51, 5.49 (1H, d, 2—OH); 5.23, 5.20 (1H, d, 3'—OH); 5.05 (1H, t, 5'—OH); 4.84, 4.83 (2H, d, $CH_2$); 4.44 (1H, m, H2); 4.11, (1H, m, H3'), 3.92 (1H, m, H4'); 3.62 (1H, m, H5'); 3.57 (1H, m, H5'); 3.41 (1H, t, CH). Characterization with mass spec. and NMR yielded data consistent with the structure of 1-propargylinosine.

One of ordinary skill in the art will appreciate that this general synthetic technique may be used to prepare various inosine molecules with substituted purine analogs and substituted ribose analogs. These inosine molecules can then be phosphorylated according to the examples given below to yield other oligo and polyribonucleotides of the present invention.

Example 2

Synthesis of 1-propargzylinosine-5'-monophosphate

Dry 1-propargylinosine (7.2g, 23.53 mmol) prepared according to the procedure of Example 1 was converted to its 5'-monophosphate as described in M. K. Yoshikawa et. al., Studies of Phosphorylation III, Selective Phosphorylation of Unprotected Nucleosides, *Bull. Chem. Soc. Japan* 42:3505–3508, yielding 10.2 g (83.2%). Samples for HRMS were obtained by cation exchange chromatography conversion of the monophosphate into its $NH_4^+$ salt. Characterization with mass spectrometry gave the following results: HRMS (glycerol) m/z Calcd. 385.05493 Obsv. 385.05122 (M—$3NH_3$—H). These results were consistent with the structure of 1-propargylinosine-5'-monophosphate.

Example 3

Synthesis of 1-propargylinosine-5'-diphosphate

Dry 1-propargylinosine-5'-monophosphate (10.2 g, 19.6), prepared according to Examples 1–2, was converted to its 5'diphosphate as described by Hoard & Ott (1965), *J Am. Chem. Soc.* 87:1785–1788. Samples for HRMS were obtained by cation exchange chromatography converting the compound into its $NH_4^+$ salt. $UV_{max}$ 250 nm, $\lambda_{max}$ 7432 (0.1 M NaCl, 0.1 M phosphate buffer pH 6.8). Characterization by mass spectrometry gave the following results: HRMS (glycerol) m/z Calcd. 465.02126 Obsv. 465.02023 (M—$3NH_3$—H). These results were consistent with the structure of 1-propargylinosine-5'-diphosphate.

Example 4

Enzymatic Synthesis of Poly(1-propargylinosinic Acid)

A solution containing the following components was incubated at 37° C. for 3 hours with gentle rocking: 0.333 ml of Tris-HCl (pH 9.0, 2M); 0.333 ml of $MgCl_2$ (0.1M); 0.333 ml of 2-mercaptoethanol (2%); 1.332 ml of $H_2O$; 14.96 IU of PNPase (*E. coli*) in 0.1 ml of buffer containing 50% glycerol, 5 mM Tris, and 0.5 mM dithiothreitol at pH 8.0; and 49.2 mg of 1-propargylinosine-5'-diphosphate (prepared according to the procedure of Examples 1–3).

After incubation, the polymer was purified from the reaction mixture by cation exchange chromatography (0.25 M Tris HCl, pH 5.5) at a flow rate of 1.32 ml/min. All hardware required for column chromatography (ie. column, fittings, tubing) had been sterilized by bathing in ethanol overnight. All fractions with 254 nm absorbance were pooled and the pH was adjusted to 7 with dilute NaOH. The aqueous solution was dialyzed against 0.1 M NaCl (12 L, 24 hours) and $H_2O$ (24 L, 48 hours). Lyophilization of the aqueous solution gave poly(1-propargylinosine) (13.9 mg, 28.3%) as a fluffy, pale yellow solid. $UV_{max}$ 250 nm, $\lambda_{max}$ 7007 (0.1 M NaCl, 0.1 M phosphate buffer pH 6.8).

Example 5

Chemical Synthesis of Oligo(1-propargylinosinic Acid)

Oligo(1-propargylinosinic acid) may be prepared as follows:

Step 1

Synthesis of 2'-O-methyladenosine

Oven dried adenosine was converted to its 2'-O-methyl analog as described earlier by Yano et al. (1980), *Biochemica et Biophysica Acta* 629:178–183. FABMS (glycerol & $H_2O$) m/z 282 ($MH^+$).

Step 2

Synthesis of 2'-O-methylinosine

Deamination of 2'-O-methyladenosine was accomplished by a modified procedure of Iwai et al., Anomeric 9-D-Glucopyranosyl-adenines and 9-D-Glucopyranosyl-hypozanthines, in *Synthetic Procedures in Nucleic Acid Chemistry* 135–142 (Zorbach & Tipson eds., Interscience Publishers, New York, N.Y., 1965). To a solution of 2'-O-methyladenosine (6.61 g, 23.5 mmol) dissolved in 4.4% aqueous acetic acid was added 13.1 g sodium nitrate (190 mmol). This reaction solution was stirred 24 hours in a foil covered vessel and thereafter evaporated to dryness in vacuo. The product was desalted with Amberlite XAD-4 resin and recrystallized in methanol. FABMS (glycerol) m/z 284 ($MH^+$).

Step 3

Synthesis of 2'-O-methyl-1-propargylinosine

Propargyl bromide (2.2 ml, 19.7 mmol) and 1,8 diazabicyclo[5.4.0]undec-7-ene (DBU) (2.7 ml, 17.7 mmol) were added to a suspension of 2'-O-methylinosine (5.4 g, 19.0 mmol) in dimethylacetamide (100 ml). The reaction mixture was stirred at room temperature under argon for 18 hours at which time an additional 1 ml of DBU was added. After 6 hours, the reaction solution was evaporated in vacuo to an oil and dried onto 20 g of silica gel. Pure product was isolated by silica gel chromatography with a 2–5% gradient of methanol in chloroform. FABMS (glycerol & methanol) m/z 321 ($MH^+$). 1H-NMR (DMSO-d6): 8.50 (1H,s, H2); 8.41 (1H, s, H8); 5.96 (1H, d, H1'); 5.28 (1H, d, 2'—OH); 5.09 (1H, t, 5'—OH); 4.82 (2H, s, $CH_2$); 4.27 (2H, m, H2', H3'); 3.94 (1H, m, H4'); 3.60 (2H, m, H5', H5"); 3.41 (1H, s, CH).

Step 4

Synthesis of 5'-DMTr-2'-O-methyl-1-propargylinosine

Dry 2'-O-methyl-1-propargyl inosine was protected at the 5'-OH position as described earlier by Tutonda et al. (1998), *J Med. Chem.* 41:4958–4964. FABMS (glycerol, 1% TFA & methanol) 623 (MH+).

Step 5

Synthesis of 5'-DMTr-2'-O-methyl-3'-phosphoroamidite-1-propargylinosine

Dry 5'-DMTr-2'-O-methyl-1-propargylinosine was converted to its phosphoramidite by a modified procedure of Tutonda et al. (1998), *J Med. Chem.* 41:4958–4964. To a mixture of 3 g 5'-DMTr-2'-O-methyl-1-propargylinosine (4.8 mmol) and 248.3 mg diisopropylammonium tetrazolide (1.4 mmol) in 36 ml acetonitrile, was added 2.1 ml 2-cyanoethyl tetraisopropyl phosphorodiamidite (6.6 mmol). The reaction mixture was stirred vigorously overnight under argon at which time an additional 0.5 ml of phosphorodiamidite reagent was added. At 48 hours, the raction was quenched by adding an equal volume of saturated aqueous NaHCO$_3$ solution. The product was extracted from the aqueous solution with ethyl acetate (2×25 ml). The ethyl acetate was washed with brine (2×30 ml) and H$_2$O (2×30 ml). The ethyl acetate was dried over sodium sulfate, filtered, and evaporated. Product was purified by flash silica gel chromatography with a 0–90% gradient of ethyl acetate in a hexane. 31P—NMR (CDCN): 154.5 (1P, s); 154.4 (1P, s)

5'-DMTr-2'-O-methyl-3'-phosphoroamidite-1-propargylinosine may be used to prepare oligoribonucleotides of chain lengths 12 to 100 or longer using standard oligonucleotide synthetic techniques. For example, a 32-mer of 1-propargylinosinic acid monomers is easily prepared using an ABI synthesizer. One of ordinary skill in the art will readily appreciate that oligomers of various lengths may be prepared using standard synthetic techniques.

Example 6

Synthesis of poly(1-ethylinosinic acid)

The general synthetic steps described in examples 1–5 can be utilized, with modifications that will be readily apparent to those skilled in the art, for synthesis of other substituted ribonucleotides of the present invention. For example, poly (1-ethylinosinic acid) may be synthesized by substituting propargyl bromide with ethyl iodide in Example 1, then following analogous polymerization procedures as in Examples 4 and 5. Other 1-N substituted, 2-substituted, and 8-substituted compounds are readily prepared in substantial accordance with these examples. Similar compounds containing a thio group at the 6 position in the purine analog are easily synthesized using methods well known in the art. For example, when a nucleoside has an alkylated 1-N position and a 6-imino group, the 6-imino group may be replaced with sulfur when reacted with hydrogen sulfide. Also, nucleotides with a 6-oxo group may be converted into the 6-thio group when reacted with phosphorous pentasulfide in pyridine. By following these methods, one may synthesize other oligo- and polyribonucleotides of the present invention.

Example 7

Polymer Degradation

To a solution of poly(1-propargylinosineic acid) (prepared according to the procedure of Examples 1–4) in 0.1 M NaCl (100 μl 2 mg/ml) was added 65 μl of a solution containing the following: 33 μl of Tris-HCl (2M, pH 9.0); 44 μl of MgCl$_2$ (0.1 M), 44μ of venom phosphodiesterase, and 22 μl of alkaline phosphatase. The solution was incubated at 37° C. with a gentle rocking for 18 hours and then diluted to 5 ml with NaCl (0.1 M). TLC in SSE (EtOH:nPrOH:H$_2$O, 4:2:1) confirmed degradation to starting nucleoside 1-propargylinosine.

Example 8

Antiviral Activity

The oligo- and polyribonucleotides of the present invention have potent antiviral activity regarding both retroviruses and DNA viruses. While not being bound by any particular theory, they are intended to inhibit early stages in HIV and HCMV infection. Furthermore, the composition poly(1-propargylinosinic acid), shows no evidence of secondary structure in solution, in contrast to the previously described potent antiviral agents PMTI and TTPR-32mer. Structure-activity relationships developed in connection with PMTI and TPPR-32mer strongly supported the hypothesis that a cooperatively melting single-stranded structure was necessary for anti-HIV and anti-HCMV activity. The demonstration that poly(1-propargylinosinic acid) is equipotent to the previously synthesized sulfur-containing compounds, but shows no secondary structure in solution, suggests that this may comprise a novel structural class of antiviral drugs. The antiviral activity of these compounds against human immunodeficiency virus (HIV), and the human cytomegalovirus (HCMV) can be demonstrated by the following assays and procedures.

Biological Assays

Assays for anti-HIV activity of poly(1-propargylinosineic) prepared according to the procedure of Examples 1–4 were conducted by Dr. Robert Buckheit, Jr. of the Southern Research Institute with strains of HIV-1 and HIV-2 in various cell lines and with cell free preparations of reverse transcriptase as previously described, Broom et al. (1995), *J. Med. Chem.* 38:3253–3257. Table 1 shows the inhibitory activity (EC$_{50}$,μM, wherein the concentration of polynucleotide is based on an average molecular weight of 100,000) against the cytopathic effect of various retroviral strains of HIV in CEM-SS cells.

TABLE 1

| Virus | ddC | Poly(1-propargylinosinic acid) |
| --- | --- | --- |
| RF | 0.039 | 0.131 |
| III$_B$ | 0.0693 | 0.263 |
| SK1 | 0.0254 | 0.0444 |
| ROD | 0.0621 | 0.0579 |

Table 2 shows the inhibitory activity (EC$_{50}$) against reverse transcriptase (RT) in a cell free supernate, wherein the concentrations of poly(1-propargylinosineic acid) and PMTI are based on an average molecular weight of 100,000.

TABLE 2

| Compound | RT, EC$_{50}$ | CEM-SS (RF), EC$_{50}$ |
| --- | --- | --- |
| Poly(1-propargylinosinic acid) | 0.223 μM[a] | 0.131 μM |
| PMTI | 0.00028 μM | 0.17 μM[b] |

Assays of anti-HCMV activity were conducted by Drs. R. Sidwell and J. Huffman at Utah State University with the AD-169 strain in the MRC-5 cell line as described in Huffman et al. (1994), *Nucleosides and Nucleotides* 33:607–613. Table 3 shows the inhibitory activity against HCMV strain AD-169 in the MRC-5 cell line.

TABLE 3

| Compound | CD$_{50}$ (μg/ml)[a] | ED$_{50}$ (μg/ml)[b] | TI[c] |
| --- | --- | --- | --- |
| Poly(1-propargylinosinic acid) | 316 (3.16 μM)[d] | 1.9 (0.019 μM)[d] | 166 |
| Ganciclovir | >1000 | 2.4 (9.4 μM) | >417 |

[a]50% Cytotoxic dose.
[b]50% Effective dose.
[c]TI = CD50 ÷ ED50
[d]Concentration based on an average molecular weight of 100,000 daltons.

SUMMARY

In summary, the present invention provides novel compositions that show potent antiviral activity against both DNA and RNA viruses. In particular, the present invention provides oligo- and polyribonucleotides with potent antiviral activity against HIV and HCMV. These compositions are thought to operate in a novel fashion at an early stage of viral infection, meeting the need for alternatives or synergistic therapies to the toxic treatments currently available. The present invention discloses methods for synthesizing oligo- and polyribonucleotides showing antiviral activity.

We claim:

1. A composition comprising a number, n, of nucleoside monomers that are represented by the formula:

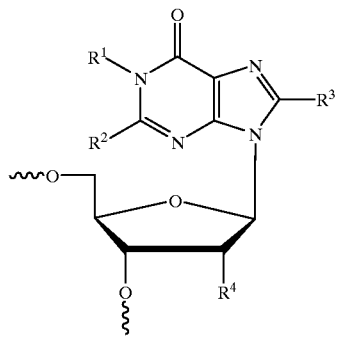

wherein $R^1$ is a member selected from the group consisting of alkyl, aralkyl, cycloalkyl, and unsaturated alkyl; $R^2$ and $R^3$ are independently selected from the group consisting of H, $SCH_3$, $NH_2$, alkylthio, and alkylamino; $R^4$ is a member selected from the group consisting of hydroxy, fluoro, alkoxy, mercaptoalkyl, alkoxyalkoxy, hydroxyalkoxy, and aminoalkoxy; n is from about 12 to 1000; and wherein the nucleoside monomers are joined by phosphodiester or phosphorothioate linkages.

2. The composition of claim 1, wherein $R^1$ is an unsaturated alkyl.

3. The composition of claim 2, wherein n is greater than 31.

4. The composition of claim 1, wherein the monomers are joined by phosphodiester linkages.

5. The composition of claim 1, wherein n is greater than 31.

6. The composition of claim 1, wherein n from about 100 to 1000.

7. A composition comprising a number, n, of nucleoside monomers that are represented by the formula:

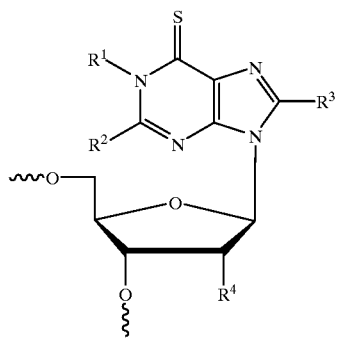

wherein $R^1$ is a member selected from the group consisting of aralkyl or cycloalkyl; $R^2$ and $R^3$ are independently selected from the group consisting of H, $SCH_3$, $NH_2$, alkylthio, and alkylamino; $R^4$ is a member selected from the group consisting of hydroxy, fluoro, alkoxy, mercaptoalkyl, alkoxyalkoxy, hydroxyalkoxy, and aminoalkoxy; n is from about 12 to 1 000; and wherein the nucleoside monomers are joined by phosphodiester or phosphorothioate linkages.

8. The composition of claim 7, wherein n is greater than 31.

9. The composition of claim 7, wherein n is from about 100 to 1000.

10. The composition of claim 7, wherein the monomers are joined by phosphodiester linkages.

11. A composition comprising a number, n, of nucleoside monomers that are represented by the formula:

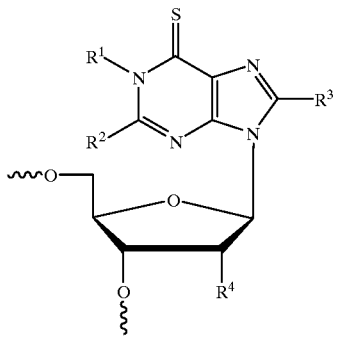

wherein $R^1$ is a member selected from the group consisting of alkyl, aralkyl, cycloalkyl, and unsaturated alkyl; $R^2$ is selected from the group consisting of $SCH_3$, alkylthio, and alkylamino; $R^3$ is selected from the group consisting of H, $SCH_3$, $NH_2$, alkylthio, and alkylamino; $R^4$ is a member selected from the group consisting of hydroxy, fluoro, alkoxy, mercaptoalkyl, alkoxyalkoxy, hydroxyalkoxy, and aminoalkoxy; n is from about 12 to 1000; and wherein the nucleoside monomers are joined by phosphodiester or phosphorothioate linkages.

12. The composition of claim 11, wherein n is greater than 31.

13. The composition of claim 11, wherein n is from about 100 to 1000.

14. The composition of claim 11, wherein the monomers are joined by phosphodiester linkages.

15. A composition comprising a number, n, of nucleoside monomers that are represented by the formula:

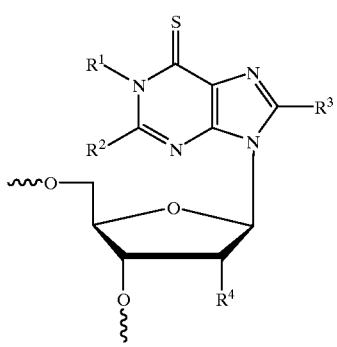

wherein $R^1$ is a member selected from the group consisting of alkyl, aralkyl, cycloalkyl, and unsaturated alkyl; $R^2$ is selected from the group consisting of H, $SCH_3$, $NH_2$, alkylthio, and alkylamino; $R^3$ is selected from the group consisting of $SCH_3$, $NH_2$, alkylthio, and alkylamino; $R^4$ is a member selected from the group consisting of hydroxy, fluoro, alkoxy, mercaptoalkyl, alkoxyalkoxy, hydroxyalkoxy, and aminoalkoxy; n is from about 12 to 1000; and wherein the nucleoside monomers are joined by phosphodiester or phosphorothioate linkages.

16. A composition comprising a number, n, of nucleoside monomers that are represented by the formula:

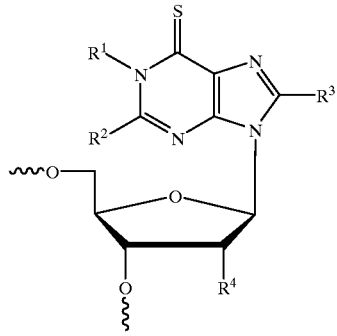

wherein $R^1$ is a member selected from the group consisting of alkyl, aralkyl, cycloalkyl, and unsaturated alkyl; $R^2$ and $R^3$ are independently selected from the group consisting of H, $SCH_3$, $NH_2$, alkylthio, and alkylamino; $R^4$ is a member selected from the group consisting of fluoro, mercaptoalkyl, alkoxyalkyl, hydroxyalkoxy, and aminoalkoxy; n is from about 12 to 1000; and wherein the nucleoside monomers are joined by phosphodiester or phosphorothioate linkages.

17. Oligonucleotides and polynucleotides comprising a number, n, of nucleoside monomers that are represented by the formula:

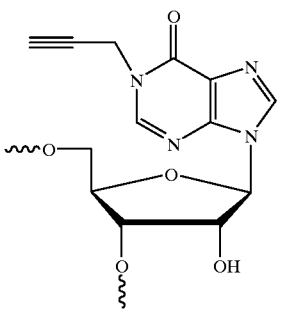

wherein n is from about 12 to 1000 and the nucleoside monomers are joined by phosphodiester linkages.

18. The oligonucleotides and polynucleotides of claim 17, wherein n is from about 100 to 1000.

19. A method of making poly(1-propargylinosinic acid) comprising the steps of:
   (a) reacting propargyl bromide, 1,8-diazabicyclo[5.4.0]undec-7-ene, and inosine to produce 1-propargylinosine;
   (b) converting 1-propargylinosine to 1-propargylinosine-5'-monophosphate;
   (c) converting 1-propargylinosine-5'-monophosphate to 1-propargylinosine-5'-diphosphate; and
   (d) polymerizing 1-propargylinosine-5'-diphosphate with polynucleotide phosphorylase to produce poly(1-propargylinosinic acid).

20. A composition prepared according to the method of claim 19.

* * * * *